(12) United States Patent
Gregory et al.

(10) Patent No.: US 7,730,761 B2
(45) Date of Patent: Jun. 8, 2010

(54) PRODUCING STRESS ON SURFACES

(75) Inventors: Walter Jay Gregory, Churchville, PA (US); Nilesh Shah, Maple Glen, PA (US); Theodore Tysak, Ambler, PA (US)

(73) Assignee: Rohm and Haas Company, Philadelphia, PA (US)

( * ) Notice: Subject to any disclaimer, the term of this patent is extended or adjusted under 35 U.S.C. 154(b) by 2 days.

(21) Appl. No.: 11/807,445

(22) Filed: May 29, 2007

(65) Prior Publication Data
US 2008/0000285 A1    Jan. 3, 2008

Related U.S. Application Data

(60) Provisional application No. 60/814,140, filed on Jun. 16, 2006.

(51) Int. Cl.
*G01N 3/56* (2006.01)
(52) U.S. Cl. .......................................................... 73/7
(58) Field of Classification Search ...................... 73/7, 73/866
See application file for complete search history.

(56) References Cited

U.S. PATENT DOCUMENTS

| | | | |
|---|---|---|---|
| 2,966,790 A | | 1/1961 | Walker |
| 3,641,807 A | | 2/1972 | Brooks |
| 4,444,882 A | | 4/1984 | Shimizu |
| 4,446,717 A | * | 5/1984 | Johanson et al. .................. 73/7 |
| 5,465,605 A | | 11/1995 | Smith |
| 5,522,251 A | * | 6/1996 | Scott ................................ 73/7 |
| 5,563,329 A | | 10/1996 | Smith |
| 5,804,706 A | * | 9/1998 | Williston ....................... 73/78 |
| 6,035,715 A | | 3/2000 | Porter |
| 6,401,058 B1 | | 6/2002 | Akalin |

FOREIGN PATENT DOCUMENTS

| | | |
|---|---|---|
| DE | 1030586 | 5/1958 |
| JP | 08-248024 | 9/1996 |
| JP | 09184797 | 7/1997 |
| JP | 11-108823 | 4/1999 |
| JP | 2002-318203 | 10/2002 |
| JP | 2003083862 | 3/2003 |
| JP | 2005-091089 | 4/2005 |

OTHER PUBLICATIONS

Harper, "The abrasion resistance of flooring materials, a review of methods of testing", Wear, vol. 4, pp. 461-478, (1996).
Kuisma, et. al., "A practical testing procedure for durability studies of resilient floor coverings", Wear, vol. 258, No. 5-6, pp. 826-834, 2005.
Kuisma, et. al., "A practical testing procedure for floor coverings: Cleanability and resistance to chemical and mechanical wear," vol. 41, No. 1, pp. 25-30, Jan.-Feb. 2003.
Redsven, et. al., "Application of a proposed standard for testing soiling and cleanability of . . . ", Tenside Surfactants Detergengents, v.40, No. 6, pp. 346-352 Nov.-Dec. 2003.

* cited by examiner

*Primary Examiner*—Hezron Williams
*Assistant Examiner*—Mark Shabman
(74) *Attorney, Agent, or Firm*—Carl P. Hemenway

(57) ABSTRACT

An apparatus for producing stress on a surface, comprising one or more service assembly and one or more cleaning assembly. The service assembly comprises one or more means for applying dirt to said surface, or one or more means for scuffing said surface, or one or more means for dragging a test material across said surface, or a combination thereof. The cleaning assembly comprises one or more scrubber, or one or more burnisher, or a combination thereof.

Also provided is a method of testing a surface with such an apparatus.

17 Claims, 4 Drawing Sheets

PRODUCING STRESS ON SURFACES

This application claims the benefit of priority under 35 U.S.C. §119(e) of U.S. Provisional Patent Application No. 60/814,140 filed on Jun. 16, 2006.

BACKGROUND

When a surface is exposed to stress, the quality of that surface often declines. The durability of a surface is its ability to resist such a decline in quality when exposed to stress. The quality of a surface may be, for example, its appearance, strength, integrity, other property or properties, or a combination thereof. Stress on a surface may arise, for example, from mechanical forces, chemicals, radiation, erosion, wear, other form or forms of stress, or a combination thereof.

In some situations, when an item is put into use, at least one of its surfaces is exposed to stress during the conditions of normal use, and the quality of that surface declines relatively slowly. It is often desired to find a way to predict, without actually exposing a given surface to normal use for a long period of time, the extent and type of degradation in quality that that surface will experience if it were to be exposed to normal use for a long period of time (i.e., two weeks or more; or 30 days or more; or 60 days or more). One way to make such a prediction accurately is to expose a surface to conditions of stress that cause the quality of the surface to degrade relatively quickly, in a way that mimics the degradation caused by the conditions of normal use. In some situations, use includes various causes of stress, including, for example service and cleaning. Service includes the various conditions other than cleaning operations to which the surface is exposed.

For example, U.S. Pat. No. 5,522,251 describes a device in which a sample of carpet or carpet tile on a rotating table is exposed to the following: a wear-causing device that rolls caster wheels over the carpet sample, a shampoo head, a dryer, a vacuum extraction head, and a carpet sweeper. It is desired to provide an apparatus that exposes surfaces to service-type conditions (i.e., conditions that reproduce normal service conditions or that mimic the effects of normal service conditions) as well as to cleaning-type conditions (i.e., conditions that reproduce normal cleaning conditions or that mimic the effects of normal cleaning conditions). In some cases, it is further desired to provide an apparatus that has one or more of the following advantages: the exposure to service-type conditions and the exposure to cleaning-type conditions can be controlled independently of each other; the apparatus can be controlled with a computer program; the sample of surface is moved linearly; or any combination thereof.

STATEMENT OF THE INVENTION

In a first aspect of the present invention, there is provided an apparatus for producing stress on a surface, said apparatus comprising one or more service assembly and one or more cleaning assembly,
  (a) wherein said service assembly comprises one or more means for applying dirt to said surface, or one or more means for scuffing said surface, one or more means for dragging a test material across said surface, or a combination thereof, and
  (b) wherein said cleaning assembly comprises one or more scrubber, or one or more burnisher, or a combination thereof.

In a second aspect of the present invention, there is provided a method of testing a surface with the apparatus of the first aspect of the present invention comprising the steps of (i) one or more times, using said service assembly to apply dirt to said surface, or to scuff said surface, or to drag a test material across said surface, or a combination thereof, and
  (ii) one or more times, using said cleaning assembly to scrub said surface, or to burnish said surface, or a combination thereof.

DETAILED DESCRIPTION

The practice of the present invention involves applying stress to a surface. The surface may be useful as part of an article or as part of a structure. Independently, the surface may be useful in an outdoor setting or in an indoor setting or in a combination thereof. Surfaces useful in outdoor settings include, for example, exterior walls, roofs, and paved surfaces. Surfaces useful in indoor settings include, for example, floors, walls, and ceilings. Independent of its location or use, the surface may be smooth or rough or textured or fibrous or any combination thereof. Some examples of suitable surfaces are those that are useful on floors, such as, for example, carpet, polymeric materials (such as, for example, vinyl), linoleum, other resilient materials, ceramic, stone, wood, laminate, coated versions thereof, and combinations thereof.

In some embodiments, the surface used in the practice of the present invention is a coating. That is, in such embodiments, the surface of interest is the coating, independent of the substrate on which the coating exists or the use to which the coated substrate will be put. For example, some coated substrates of interest are coated materials suitable for flooring including, for example, vinyl, linoleum, and other resilient materials. In some embodiments, the coating includes a polymeric material such as, for example, urethane polymer or acrylic polymer. Independent of composition, suitable coatings may be permanent or removable. Some suitable coatings are also referred to as polishes. For example, some suitable coatings contain acrylic polymer with carboxyl functionality and also contain one or more multivalent metal ion. In some embodiments, a compound that includes wax may be applied as a layer on top of a polymeric coating or instead of a polymeric coating.

Some service-type conditions involve contact between dirt and the surface of interest. Dirt is any undesired material that comes in contact with the surface of interest. Typically, dirt is particulate; normally, 90% or more of the particles are 1 mm or less in size, though the particles may sometimes agglomerate into larger clumps, especially if the dirt is wet. Dirt may contain inorganic material or organic material or a mixture of both. Dirt may originate outdoors, for example as soil, or it may originate indoors.

The practice of some embodiments of the present invention involves contacting dirt with the surface of interest. In some embodiments, the dirt used in the practice of the present invention (herein called "test dirt") is chosen to be similar to the dirt that will contact the surface of interest during conditions of actual use (herein called "actual dirt"). In some embodiments, the test dirt is chosen to have composition similar or identical to the expected actual dirt. Independent of composition, in some embodiments, the test dirt is chosen to have similar or identical effect on the surface of interest to the effect caused by the expected actual dirt; in some of such embodiments, the effect caused by the test dirt will happen relatively quickly in comparison to the effect caused by actual use.

In some embodiments that use test dirt, the test dirt contains one or more of carbon black, diatomaceous earth, and oxides. Diatomaceous earth, if used, may be plain, calcined, flux-calcined, or a mixture thereof. In some embodiments, the test dirt contains diatomaceous earth; in some of such embodiments, the diatomaceous earth includes flux-calcined diatomaceous earth. Among embodiments that use diatomaceous earth, the amount of diatomaceous earth may be, for example, by weight based on the weight of test dirt, 10% or more; or 20% or more; or 40% or more. Independently, among embodiments that use diatomaceous earth, the amount of diatomaceous earth may be, for example, by weight based on the weight of test dirt, 90% or less; or 75% or less; or 60% or less.

In some embodiments that use test dirt, the test dirt may contain one or more oxides that are separate from any oxides that may be present in any diatomaceous earth (if any) that is present. Suitable oxides, if used, include, for example, oxides that are solid at 25° C., including, for example, one or more oxide of an element selected from group IIA or B or IVB or VB or VIB or VIIB or VIII or IB or IIB or IIIA or IVA or a mixture thereof. Some suitable oxides include, for example, oxides of one or more of silicon, iron, aluminum, calcium, magnesium, and titanium. Among embodiments that use oxides, the amount of oxides may be, for example, by total weight of all oxides based on the weight of test dirt, 10% or more; or 20% or more; or 40% or more. Independently, among embodiments that use oxides, the amount of oxides may be, for example, by total weight of all oxides based on the weight of test dirt, 90% or less; or 75% or less; or 60% or less.

In some embodiments that use test dirt, the dirt is held in a container until it is desired to bring a portion of the dirt into contact with the surface of interest. When a portion of dirt is brought into contact with the surface of interest, that portion of dirt may be released from the container and fall to the surface of interest by gravity, or that portion of dirt may be mechanically conveyed to the surface of interest, for example by a mechanical device (such as, for example, a moving belt, moving hopper, rotating screw, or other conveying device) or by a stream of fluid (such as, for example, air or water or other fluid). Dirt may be brought into contact with the surface of interest, for example, by any one or any combination of these methods. In some embodiments in which dirt is released from the container, the release may be accomplished by pushing the dirt out of the container or by creating an opening in the container to let dirt fall out, or a combination thereof. In some embodiments in which an opening in the container is created, the opening may be created by opening a door, which may, for example, be a hinged door or a sliding door or a sphincter or another type of door or a combination thereof. In some of such embodiments, the opening may be on the side of the container or the bottom of the container, including embodiments in which the entire bottom of the container is an opening covered by a hinged door.

In some embodiments in which a door is opened to release test dirt from a container, the door may be operated by hand or by a mechanical device. In some embodiments, such a door is used and is operated by a mechanical device that is controlled by a computer.

In some of the embodiments in which test dirt is kept in a container, an agitator may be used inside the container. An agitator is any moving device, such as a vibrating device or rotating device. The motion of an agitator can, in some cases, keep the dirt free-flowing. The motion of an agitator can be powered by any power source, such as, for example, by hand, by a motor, or a combination thereof.

In some embodiments that use test dirt, while the dirt is in contact with the surface of interest, a mechanical force is applied to push the dirt into closer contact with the surface of interest, to drag the dirt along the surface of interest, or any combination thereof. The mechanical force may be applied by hand or by machine, using any type of material in contact with the surface of interest, including, for example, rubber, fabric, metal, wood, plastic, or a combination thereof. The force may be applied using any type of tool, including, for example, one or more roller, one or more squeegee, one or more bar, one or more rod, or a combination thereof.

Test dirt may be brought into contact with the surface of interest by any method, including, for example, dropping, blowing, spraying, spreading, throwing, or combination thereof. In some embodiments, dirt is held in a container above the surface of interest and dirt is allowed to fall onto the surface of interest through an opening in the container. For example, the bottom of the container may have an opening, and the opening may be covered by a flap that holds the dirt in the container until the flap is moved away from the opening; in such embodiments, the flap may be operated manually or mechanically, including automatically or under computer control. When the flap is moved to allow dirt to fall, it may be moved away from the opening for a time and then placed back over the opening, or it may moved away from the opening and then replaced relatively quickly two or more times.

Among embodiments in which test dirt is brought into contact with the surface of interest, the dirt may be in contact with the surface of interest without the presence of additional water (i.e., water in addition to the moisture content of the dirt itself). In some embodiments, water is present in contact with the surface of interest at the same time as test dirt. If water is present, it may be applied to the surface of interest before the dirt is brought into contact with the surface of interest, at the same time the dirt is brought into contact with the surface of interest, after the dirt is brought into contact with the surface of interest, or a combination thereof. Among embodiments in which water is present, it may be applied by any means, including, for example, spraying, pouring, misting, dropping, other means, or any combination thereof.

Among embodiments that use test dirt, the dirt may be allowed to rest in contact with the surface of interest without the application of mechanical force, or, in some embodiments, one or more mechanical device may be used to push the dirt against the surface of interest, to push the dirt across the surface of interest, or a combination thereof. Such a mechanical device might be a roller, a pad, other device, or a combination thereof. Such a mechanical device may have any type of surface including, for example, rubber, plastic, wood, metal, cloth, or a combination thereof. The surface of such a mechanical device may be smooth or rough; independently it may be porous or nonporous; independently it may be absorptive of water or not absorptive of water.

In some embodiments, test dirt is used, water is present on the surface of interest, and the dirt is acted upon by a roller. In such embodiments, the roller is brought into contact with the surface of interest in such a way that it pushes the dirt against the surface of interest. The roller may rotate through a partial cycle, a full cycle, or more than one cycle. The roller may rotate in one direction or it may alternate rotation direction one or more times. Independent of whether it rotates, the roller may also move across the surface of the surface of interest, either because the surface is moved, because the surface of interest is moved, or a combination thereof.

Another stress to which surfaces are subject during actual use is scuffing. As used herein, "scuff" means to move or remove some portion of the material of the surface of interest. For example, when a moving object makes a sudden contact with a surface, the contact sometimes deforms the surface; for example, the contact may create one or more new feature on the surface, such as, for example, an indentation, a crater, a groove, a trough, another feature, more than one of any of these, or any combination thereof. In some cases, the sudden contact may also cause some material to be removed from the surface. Independently, in some cases, the contact may cause some transfer of material from the moving object to the surface. The deformation of, or removal of material from, the surface sometimes creates a surface feature that is visible and is called a scuff mark. If the moving object also leaves behind some material that is a different color from the color of the surface, then the scuff mark is even more easily visible. In some cases, the contact that causes a scuff mark does not transfer any material from the moving object to the surface of interest. In other cases, such contact not only causes a scuff mark but also transfers material from the moving object to the surface of interest, and so the contact causes both scuffing and contact of the surface of interest with dirt.

One example of scuffing that sometimes arises during conditions of actual use comes from the contact of the heel of a shoe with the surface of a coating on a floor. Sometimes, such a contact only deforms the coating, or only removes a portion of material from the coating, or a combination thereof, without transfer of any visible material from the heel of the shoe to the coating on the floor. Such contacts are known sometimes to create scuff marks. In some cases, contact of the heel of a shoe with the surface of a coating on a floor not only causes a scuff mark but also causes material to transfer from the heel to the surface; in such cases, contact between a heel of a shoe and a surface of interest causes both scuffing and contact of the surface of interest with dirt.

In some embodiments, scuffing is performed by contacting an object made of rubber with the surface of interest. The rubber may be, for example, natural rubber, synthetic rubber, or a combination thereof. One suitable type of synthetic rubber is polyurethane rubber. Suitable rubber may have any hardness. The hardness of rubber is usually measured using a Durometer. In some embodiments, rubber is used that has Durometer hardness on the Shore A scale of 5 or higher; or 35 or higher; or 60 or higher; or 80 or higher. In some embodiments rubber is used that has Durometer hardness on the Shore A scale of 100 or lower.

In embodiments that involve scuffing, an object may be brought into contact with the surface of interest in any way, including, for example, dropping, pushing, or throwing, or any combination thereof. Any of these ways may be performed manually or mechanically, including automatically or under the control of a computer. The object may have any shape, including, for example, cylindrical, spherical, rectangular solid, flat sheet, or irregular.

In some embodiments, the scuffing is performed by bringing an object into sudden contact with the surface of interest at the same time the surface of the object is in motion in a direction that is across (rather than toward) the surface of interest. One embodiment that accomplishes this combination of motions is as follows. In some embodiments, one or more cylindrical object is used to provide scuffing. In some of such embodiments, the cylindrical object is held away from the surface of interest with its axis parallel to the surface of interest; the cylindrical object is driven so that it rotates around its own axis, and (keeping the axis of the cylindrical object parallel to the surface of interest), the spinning cylindrical object is brought into contact with the surface of interest In some of such embodiments, the driving force is applied to the cylindrical object until the desired spinning rate is achieved, and then the driving force is removed so that the spinning continues freely, and then the cylindrical object is brought into contact with the surface of interest.

In some embodiments, scuffing is performed by bringing more than one object into contact with the surface of interest simultaneously. If plural objects are used, they may be the same as each other or different. For example, two or more disks could be driven to spin and then dropped, while spinning, onto the surface of interest. The disks could be made of the same material as each other or of different materials.

Another example of a type of stress to which surfaces are subject during actual use arises when an object is placed against the surface and then dragged across the surface. Such stress occurs in actual use, for example, when a heavy object is placed on a floor surface and then is pushed or pulled across the floor.

In some embodiments of the present invention, test materials can be forced against a surface of interest, and then, while the force is applied, the test material may be dragged across the surface of interest, either by moving the test material or by moving the surface of interest, or both. In some embodiments, such motion is linear rather than rotary. In some embodiments, the speed of such linear motion, if such linear motion is used, may be 0.1 cm/sec or more; or 0.3 cm/sec or more; or 1 cm/sec or more; or 3 cm/sec or more; or 10 cm/sec or more. Independently, in some embodiments, if such linear motion is used, the speed is 300 cm/sec or less; or 100 cm/sec or less; or 30 cm/sec or less. Such linear motion, if used, may be in one direction or may be alternately in one direction and the opposite direction, optionally repeated one or more times.

In embodiments in which a test material is dragged across a surface of interest, the test material may be any type of material. Suitable test materials include, for example, woods, metals, rubbers, fabrics, plastics, abrasive materials, leathers, and combinations thereof. Test materials may have a relatively flat surface or may have an uneven surface. Some test materials include, for example, rubber sheet, leather sheet, sandpaper, cardboard, and combinations thereof. When a sheet is used, in some embodiments, the sheet of test material is attached to a rigid, flat supporting object. Sheets of test material may be attached to rigid, flat supporting objects by adhesives, clamps, fasteners, other means or by combinations thereof.

In embodiments in which a test material is dragged across the surface of interest, the dragging is performed by a dragging assembly. The pushing of the test material against the surface of interest and the dragging of the test material across the surface of interest may each, independent of each other, be performed manually or mechanically, including automatically (for example, under the control of a computer program).

In some embodiments, a sheet of test material is clamped onto a rigid, flat supporting object. In some of such embodiments, the rigid, flat supporting object may be attached to one or more actuators (such as, for example, pneumatic pistons). Among embodiments in which one or more pneumatic pistons are attached to the rigid, flat supporting object, in some cases the pneumatic pressure may be used to bring the test material into contact with the surface of interest, and, optionally, the pneumatic pressure may also be used to provide the force that presses the test material against the surface of interest during the dragging process. In some of such embodiments, more than one such pneumatic piston may be used; it is contemplated that, in such embodiments, the force that presses the test material against the surface of interest may be adjusted by adjusting the number of such pneumatic pistons that are active.

If a dragging assembly is used, it may be used in addition to or instead of applying dirt to the surface of interest. Independently, if a dragging assembly is used, it may be used in addition to or instead of scuffing the surface of interest.

Embodiments of the service assembly of the present invention are contemplated in which any one, any two, or all three of the following are used: applying dirt, scuffing, and dragging test material across the surface of interest.

In some embodiments, the practice of the present invention involves the use of one or more scrubber. A scrubber is a device that "scrubs" a surface (i.e., that applies force to a surface in a manner that is oscillatory or rotary or a combination thereof). Scrubbing is done in the presence of one or more fluid. Fluid may be applied to the surface by any method, including, for example, dropping, blowing, spraying, spreading, throwing, or combination thereof. The fluid may be applied to the surface by hand, by a device that is present in addition to the scrubber, by a device that is a part of the scrubber, or a combination thereof. Suitable fluids may be aqueous or non-aqueous. Aqueous fluids contain 50% or more water by weight, based on the weight of the fluid. In some embodiments, at least one aqueous fluid is used. Independently, in some embodiments, one or more fluid is used that contains one or more surface-active agent. The portion of the scrubber that applies force to the surface of interest may be any shape and any material. For example, the portion of the scrubber that applies force to the surface of interest may include a woven fabric, a nonwoven fabric, a felt, a brush, or any combination thereof. In some embodiments, the scrubber may use a pad, drum, or brush that rotates or oscillates; any geometry of pad, drum, or brush may be used to scrub the surface of interest. For example, in some embodiments, the scrubber includes one or more cylindrical brush that rotates around the cylinder axis, with that axis held parallel to the surface of interest, with the bristles roughly perpendicular to the axis, and with the ends of the bristles touching the surface of interest.

In some embodiments, scrubbers use one or more rotating pad or drum or brush that rotates at 10 revolutions per minute (rpm) or faster; or 50 rpm or faster; or 100 rpm or faster. Independently, in some embodiments, scrubbers use one or more rotating pad or drum or brush that rotates at 1000 rpm or slower; or 500 rpm or slower; or 300 rpm or slower.

In some embodiments, a scrubber, if used, is optionally additionally equipped with one or more means for removing fluid from the surface of interest, including, for example, one or more wiping device, one or more suction device, or both. Some suitable wiping devices are made, for example, of flexible material such as, for example, natural or synthetic rubber. One suitable wiping device is a squeegee. Wiping device, if present, may be operated by hand or mechanically, including automatically or under control of a computer. Suction device, if present, may be operated by hand or mechanically, including automatically or under control of a computer.

In some embodiments, the practice of the present invention involves one or more burnisher. A burnisher is a device that burnishes a surface. A surface is burnished by forcing an object along the surface while also pushing the object against the surface. For example, an object used for burnishing may be a fibrous pad. Usually, the fibrous pad is a relatively thin, flat disk, and the burnisher rotates the disk around its own axis, with that axis held perpendicular to the surface of interest. Normally, burnishing is done without the presence of fluid. Among embodiments that use a burnisher with a rotating pad, the pad rotates at 250 rpm or higher; or 500 rpm or higher; or 1000 rpm or higher. Independently, among embodiments that use a burnisher with a rotating pad, the pad rotates at 20,000 rpm or lower; or 10,000 rpm or lower, or 5,000 rpm or lower.

While the present invention is not limited by any specific theory, it is considered that, when some burnishers rotate a burnishing pad at relatively high rates, a region of reduced pressure is created between the pad and the surface of interest, and thus the surrounding ambient atmospheric pressure causes the burnishing pad to be pushed against the surface of interest. Some burnishers are provided with springs that pull up on the burnishing pad and the motor that drives the burnishing pad. In some of such burnishers, the springs are adjustable, so that the force of the burnishing pad against the surface of interest may be changed in order to provide the desired amount of force that pushes the burnishing pad against the surface of interest during the operation of the burnisher.

In some embodiments, the apparatus further includes a measurement assembly. A measurement assembly is an apparatus that includes a device for measuring the quality of the surface of interest. Such a device might measure any property, for example, optical properties, mechanical properties, chemical properties, and combinations thereof. Some suitable optical properties include, for example, appearance properties (such as, for example, color, gloss, brightness, or combinations thereof), spectral properties (such as, for example, absorption spectra, reflectance spectra, transmission spectra, or combinations thereof; including, for example, spectra in the infrared, visible, or ultraviolet regions, or combinations thereof), or combinations thereof. Suitable mechanical properties include, for example, smoothness, coefficient of friction, hardness, modulus, mechanical damping, sound damping, and combinations thereof. Chemical properties include, for example, composition, reactivity, surface tension, and combinations thereof.

A device for measuring the quality of a surface, if included, may be operated by hand or automatically, including, for example, operated by a computer. For example, in some embodiments, the surface of interest is held horizontally, facing upward, and a device for measuring the quality of the surface could be held above the surface of interest. If necessary, the device could be brought close to the surface for the purpose of making a measurement and then moved away from the surface. Independently, in some embodiments, the device could be moved horizontally, or the surface could be moved horizontally, or both, so that the device would be above a different position on the surface. In some embodiments, the device is thus moved to a variety of positions on the surface of interest, the device makes a measurement at each position, and the device stores the result of each measurement, for example by making a graph, by printing numerical results, by making a digital record, by sending data to a computer, or by a combination thereof.

The surface of interest may be brought into contact with the service assembly, the cleaning assembly and, if used, the measurement assembly by any method. In some embodiments, for example, the surface of interest is held horizontally on a track that is capable of moving the surface of interest in at least one horizontal direction. Is some of such embodiments, the surface of interest is held rigidly in a holder, and, in some embodiments, that holder is mounted on horizontal tracks, thus allowing the surface of interest to move horizontally in the direction of the tracks. The surface of interest may be held rigidly in the holder by any means, including, for example, mechanical fasteners, adhesives, double-sided tape, magnets, suction, or a combination thereof. The holder, in some embodiments, can be moved forward and backward in the direction of the tracks by the action of a motor, and the motor may, for example, be controlled manually or automatically, for example by a computer.

In some embodiments in which the surface of interest can be moved horizontally forward and backward along the direction of tracks, one or more of the various devices of the apparatus (such as, for example, a scrubber, burnisher, device for applying dirt, etc.) of the present invention is held fixed (i.e., it does not travel in the direction of the tracks). In such embodiments, the surface of interest can be brought near the device, for example, the surface of interest may be brought directly underneath the device. In such embodiments, the surface may be raised or the device lowered, or both, to bring the device and the surface of interest into contact, if necessary for the device to operate properly.

In some embodiments, the only item that moves horizontally is the surface of interest, in its holder. The surface of interest is brought:to each desired device, the device is operated as desired, and then the surface of interest is brought to the next device. In this way, the apparatus of the present invention may be operated in a wide variety of ways. For example, the surface of interest could be exposed to application of dirt followed by scrubbing, and this pattern, if desired, could be repeated multiple times. The surface of interest could be exposed to any desired mixture of events including, for example, exposure to dirt, scuffing, scrubbing, burnishing, or combinations thereof, including repetitions of one or more events and repetitions of a sequence of two or more events. It is contemplated that if a measurement assembly is used, the surface of interest may, for example, be measured by the measurement assembly, then exposed to one or more operation of a service assembly and one or more operation of a cleaning assembly, and then measured again by the measurement assembly. Also contemplated are embodiments in which multiple operations of the measurement assembly are performed on the surface of interest, interspersed among multiple repetitions of operations of one or more service assembly, multiple operations of one or more cleaning assembly, or both.

It is contemplated that, in some embodiments, each function within the apparatus of the present invention can be controlled independently of the other functions. For example, embodiments are contemplated in which the service assembly can be controlled independently of the cleaning assembly. For example, in such embodiments, an operator could increase (or decrease) the amount of time to which a surface of interest is exposed to the operation of the service assembly without necessarily changing the amount of time to which the surface of interest is exposed to the operation of the cleaning assembly. For another example, in such embodiments, an operator could increase (or decrease) the amount of time to which a surface of interest is exposed to the operation of the cleaning assembly without necessarily changing the amount of time to which the surface of interest is exposed to the operation of the service assembly. Also contemplated are embodiments in which independent change to one or more individual functions (e.g., dirt application and scuffing) within the service assembly could be made without necessarily making any changes to other individual functions within the service assembly. Similarly, embodiments are contemplated in which independent change to one or more individual functions (e.g., scrubbing and burnishing) within the cleaning assembly could be made without necessarily making any changes to other individual functions within the cleaning assembly.

It is contemplated that a computer program that controls the operation of the apparatus of the present invention would allow the practitioner to decide on any progression of events, in any order, including (where applicable) the duration of each event, and including any desired repetitions of events or repetitions of sequences of events. The practitioner could record the desired progression of events in the computer program, which could then operate the apparatus according to the recorded desires of the practitioner. It is contemplated that computer control provides one means of allowing the operator to make independent changes in one or more individual functions (e.g., dirt application, scuffing, scrubbing, and burnishing) without necessarily changing other individual functions.

For example, two or more tiles, each with a different floor polish coating, could be placed in a holder. Each tile could be measured and then exposed to the same regimen of service, cleaning, and measurement as all the other tiles. For example, each tile could be exposed to contact with dirt, removal of the dirt, scuffing, cleaning, and burnishing. After such exposure, each tile could be measured, and the entire process could be repeated, as many times as desired. The method and duration of each part of the process (contact with dirt, scuffing, cleaning, and burnishing) could be chosen to mimic the effects of exposure to normal use conditions. The details of each part of the process, including service, cleaning, and measurement, could be determined in advance, recorded in computer program, and then performed under the operation of the computer.

In embodiments involving control by a computer program, the operator would be able to easily change the conditions of the operations of the apparatus. For example, it is desired to change the amount of dirt applied to the surface of interest or the duration of scrubbing or any other part of the operation of the apparatus, such change could be implemented readily by recording the desired conditions in the computer program.

In some embodiments, it is useful to consider the test duration (i.e., the duration of time during which the surface of interest is tested with the apparatus of the present invention). The test duration is the total time for the operation of the service assembly, the cleaning assembly, the optional measurement assembly, and any other assemblies that may be additionally included in the apparatus of the present invention, including combinations thereof, if any, and repetitions thereof, if any. In some embodiments, the test duration is one week or less; or 4 days or less; or 2-days or less; or one day or less; or 12 hours or less. Independently, in some embodiments, the test duration is 10 minutes or more; or 30 minutes or more; or 1 hour or more; or 2 hours or more.

Figure 1:
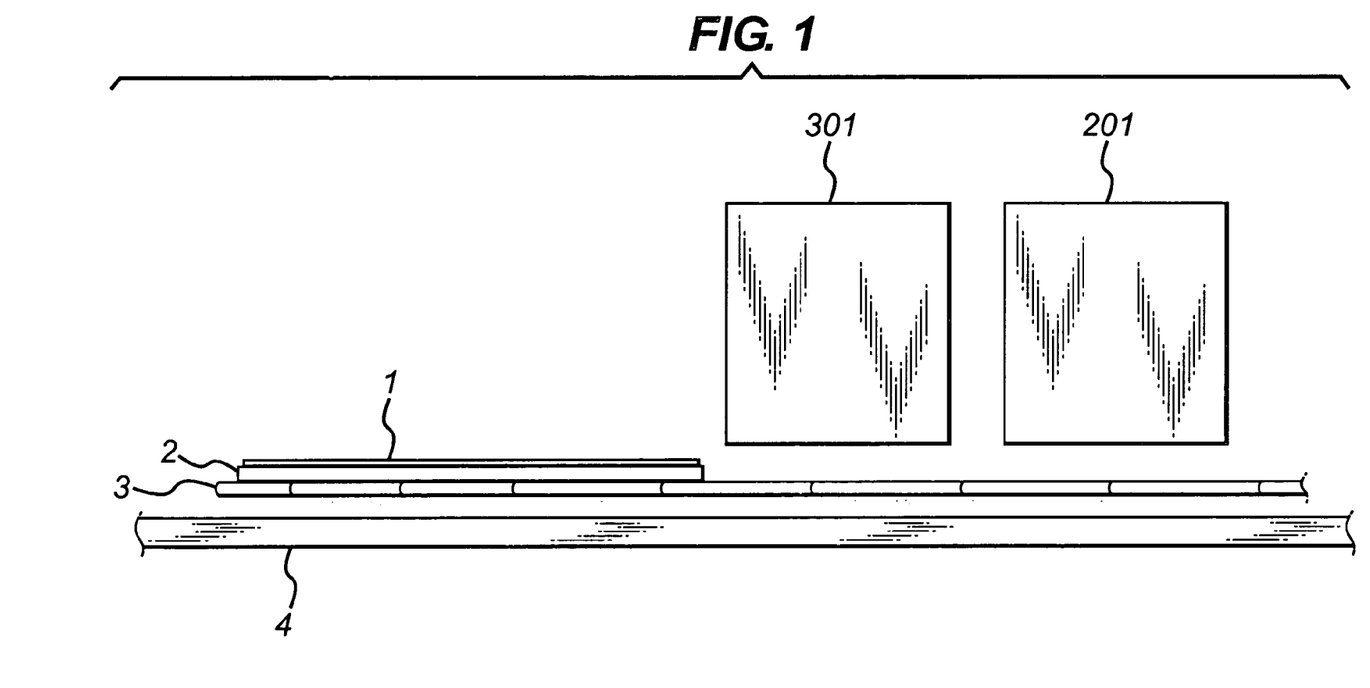
FIG. 1 is a schematic side view of one embodiment of an apparatus for producing stress on surfaces.

FIG. 1 illustrates one embodiment of the present invention. FIG. 1 is a side view; the illustrated embodiment has a "length" dimension from left to right in FIG. 1 and a "width" dimension out of the plane of the illustration. The surface of interest is a coated floor tile 1, which is held firmly in a tray 2. The tile may be held in place by any method; one suitable method is with an adhesive, for example a pressure sensitive adhesive, for example using two-sided adhesive tape. The tray 2 may be designed to hold a single tile 1 or multiple tiles 1. The tray 2 rests on rails 3. In FIG. 1, only one rail is shown; the other rail is parallel to the one shown. The tray 2 moves horizontally to the right or left by riding on the rails 3. One of the rails 3 is visible in FIG. 1; the other rail 3 is directly behind the visible rail 3. The rails 3 are held in place by rigid supports not shown in FIG. 1.

In some embodiments, the tray 2 is moved by a transport apparatus, not shown in FIG. 1, located between the rails 3; such a transport apparatus may include, for example, gears, cables, straps, or a combination thereof, operating on the bottom of the tray 2 in order to move it horizontally. It is contemplated that the transport apparatus may, in some embodiments, be driven by a motor. It is further contemplated, in some embodiments using such a motor, that the motor may be controlled by a computer.

Also in FIG. 1, rigid horizontal support member 4 is part of a larger rigid support apparatus (not shown) that holds all parts of the apparatus in place.

Figure 2:
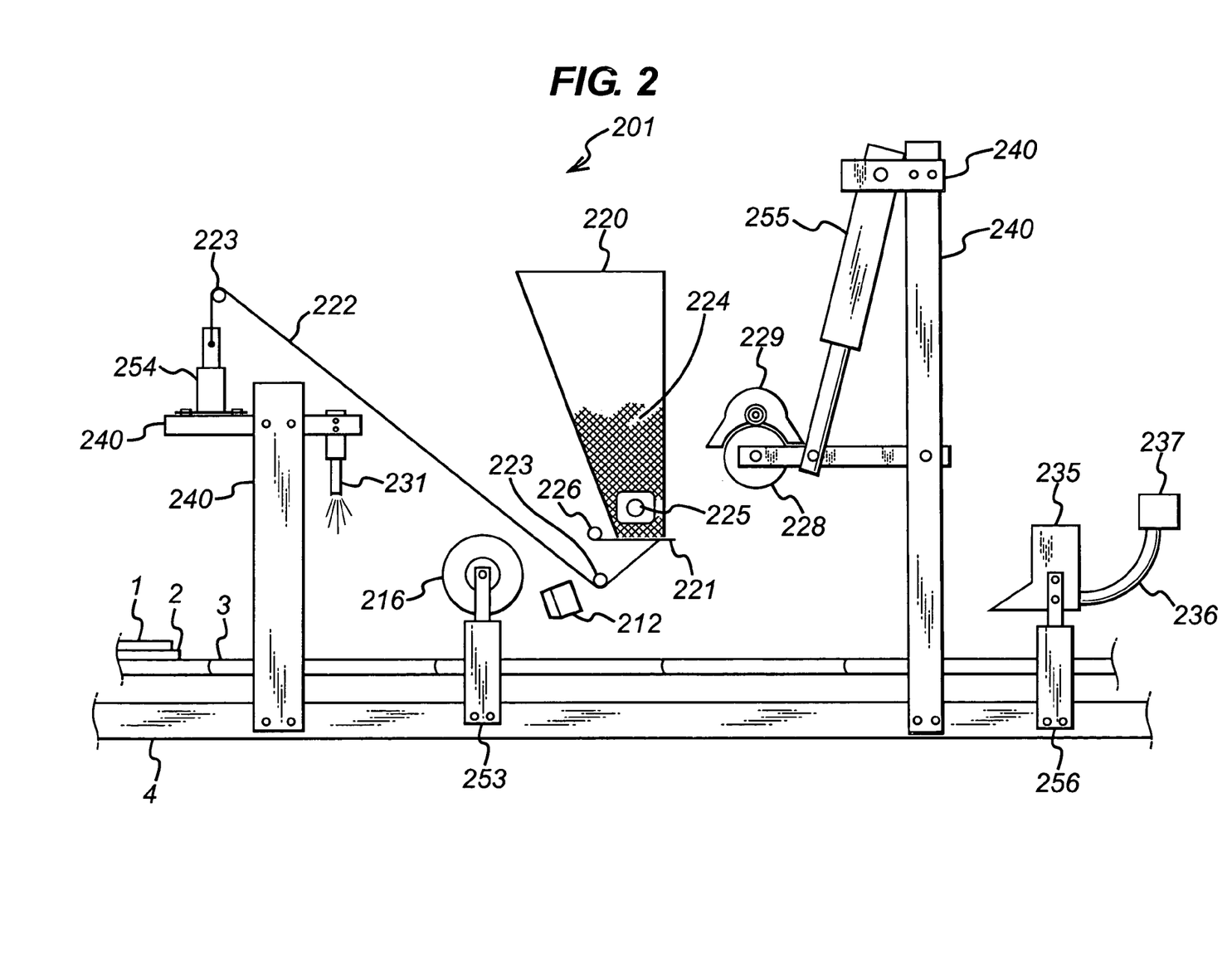
FIG. 2 is a side view of an embodiment of a service assembly.

FIG. 2 shows the details of item 201, the embodiment of a service assembly shown in FIG. 1. FIG. 2 is a side view. Rigid structural support members 240 hold various items in place above track 3. The support members 240 on the near side of the service assembly 201 are shown. Identical support members (not shown in FIG. 2) are also present on the far side of the service assembly 201. Nozzle 231 is capable of spraying water over the entire width of the surface of floor tile 1. Nozzle 231 is supplied with water by a hose from a reservoir of water, and the spray is turned on and off by a control mechanism, in this embodiment controlled by a computer (water reservoir, hose, and control mechanism are not shown in FIG. 2). The water that is sprayed onto the surface by nozzle 231 can optionally be removed using the optional air knife 212 (which extends across the width of the service assembly 201 and is held in place by structural support members that are not shown in FIG. 2).

Also shown in FIG. 2 is an apparatus for applying dirt to the surface of floor tile 1. In the illustrated embodiment, dirt is held in dirt reservoir 220. In FIG. 2, the cross section of dirt reservoir 220 is shown; dirt reservoir 220 extends across the width of the apparatus. Optionally, the dirt 224 can be stirred using agitator 225, which also extends the width of the apparatus, inside the dirt reservoir 220. Agitator 225 can optionally be driven by a motor. Dirt reservoir 220 contains dirt 224, which can be dropped onto surface of floor tile 1. In order to drop dirt 224 onto surface of floor tile 1, lever 221, which pivots on hinge 226, is pulled away from the bottom of dirt reservoir 220, and the dirt 224 can fall down. Lever 221 is pulled by cable 222, which runs over pulleys 223. Cable 222 is pulled by actuator 254. Dirt reservoir 220, lever 221, and pulleys 223 are held in place above the track 3 by support members that are not shown in FIG. 2. The actuator 254 can optionally be operated by a computer.

Also shown in FIG. 2 is an optional roller 216 for applying pressure to dirt 224 that is in contact with surface of floor tile 1, which is held in place in tray 2. Roller 216 extends across the width of service assembly 201 and is held in place above track 3 by two actuators 253, one (shown in FIG. 2) on the near side of the service assembly 201 and another (not shown in FIG. 2) on the far side of service assembly 201. After dirt 224 falls onto surface of floor tile 1, surface of floor tile 1 is moved along track 3 until the portion of surface of floor tile 1 where the dirt lies is underneath roller 216. Roller 216 may then be lowered by actuators 253 until roller 216 is in contact with surface of floor tile 1. If desired, surface of floor tile 1 can be moving along track 3 while roller 216 is in contact with surface of floor tile 1.

Also shown in FIG. 2 is an assembly for scuffing. Rubber wheel 228 is a disk with an axis length smaller than its diameter. Rubber wheel 228 is mounted so that it can spin freely on its axis. Motor 229 causes rubber wheel 228 to spin rapidly on its axis. When desired, surface of floor tile 1 is brought to a position underneath rubber wheel 228, and then the inner piston of actuator 255 extends, forcing rubber wheel 228 downward, brining rubber wheel 228 into contact with surface of floor tile 1, while motor 229 is held in place by mechanical support structures (not shown in FIG. 2). Sometimes, depending on the conditions of the test and the composition of the surface of floor tile 1, the contact between rubber wheel 228 and surface of floor tile 1 will cause the creation of a scuff mark on surface of floor tile 1.

Also shown in FIG. 2 is an optional vacuum head 235, which extends across the width of the service assembly 201 and is held in place by two actuators 256 (the near actuator 256 is shown in FIG. 2, while the far actuator 256 is not). Air is removed from the vacuum head 235 by pump 237 through tube 236. In some embodiments, vacuum head 235 is operated to remove material from surface of floor tile 1. In some embodiments, tray 2 is moved along track 3 so that surface of floor tile 1 is underneath vacuum head 235; pump 237 may be turned on to pull air through vacuum head 235; actuators 256 may be operated to lower vacuum head 235 so that it is near surface of floor tile 1; and tray 2 may be moved so that all or part of surface of floor tile 1 is brought underneath vacuum head 235.

Each of the items in service assembly 201 may be operated manually or automatically, including operation controlled by a computer program.

Figure 4:
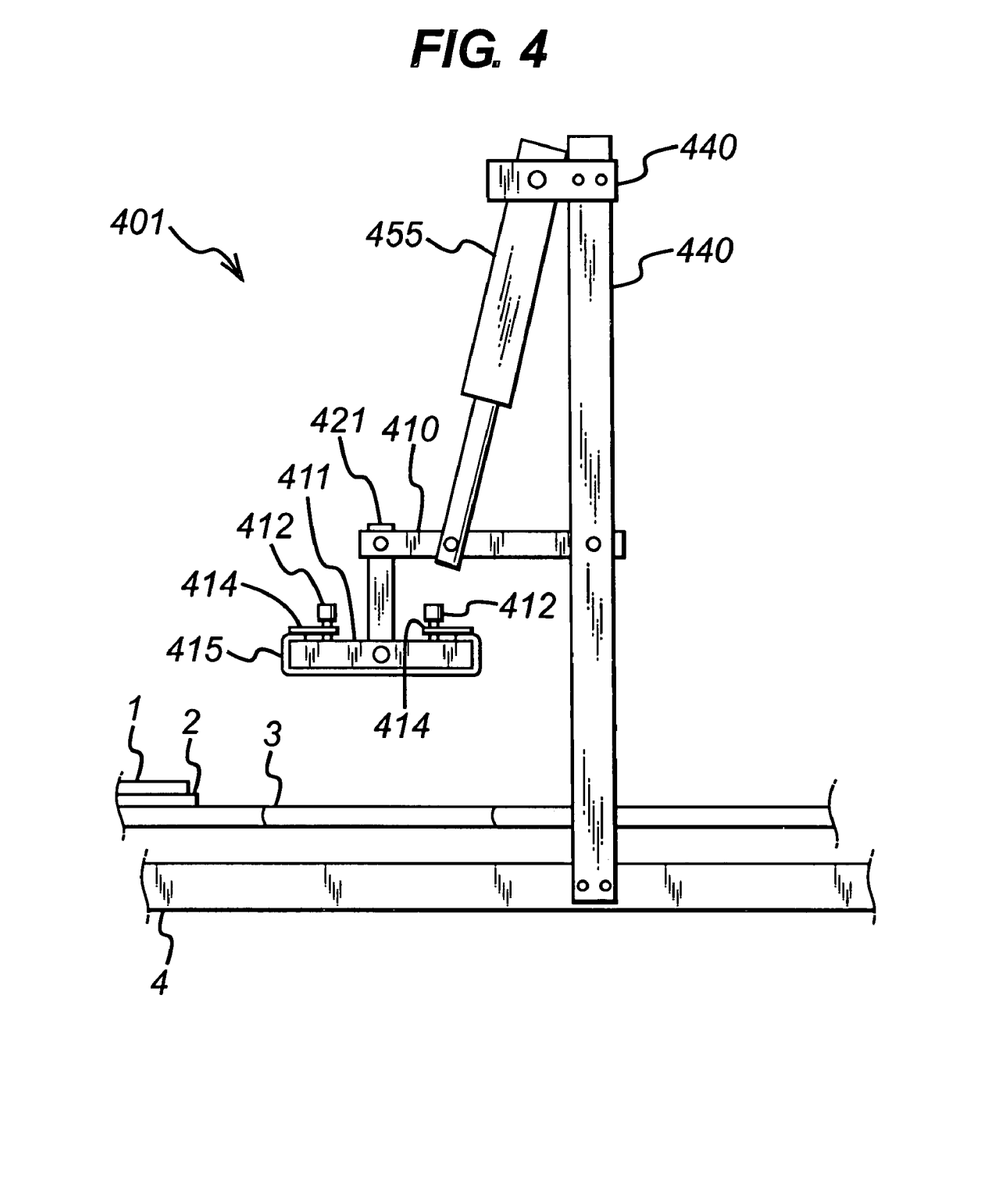
FIG. 4 is a side view of a dragging assembly.

FIG. 4 shows an embodiment of optional dragging assembly 401. Dragging assembly 401, if used, is considered part of the service assembly 201, though no dragging assembly 401 is illustrated in FIG. 2. Floor tile 1 is held in tray 2, which moves along track 3. The assembly is attached to rigid horizontal support member 4. In the embodiment illustrated in FIG. 4, the dragging assembly 401 is held in place by support members 440. Test material sheet 415 is clamped to rigid, flat supporting object 411. The clamps are constructed from rigid clamp bars 414, which are forced against the rigid, flat supporting object 411 by screws 412.

When it is desired to perform a dragging operation, floor tile 1 is brought underneath the dragging assembly 401. Then, actuator 455 extends, pushing downward on support arm 410, which pushes downward on suspending arm 421, thus forcing test material sheet 415 against the floor tile 1. Then, while the test material sheet 415 is pressing against floor tile 1, tray 2 may be moved along rail 3. This motion of tray 2 provides the action of dragging test material sheet 415 across floor tile 1.

In some embodiments, there may be plural constructions of support members 440, actuator 455, support arm 410, and suspending arm 421. These plural constructions may be placed side by side, across the width of dragging assembly 401. Only the nearest such construction is illustrated in FIG. 4. Rigid, flat supporting object 411 and test material sheet 415 extend across the width of dragging assembly 401. In some embodiments, multiple clamps (such as those constructed of rigid clamp bars 414 and screws 412) may be used; only the two nearest clamps are illustrated in FIG. 4.

Each of the items in dragging assembly 401 may be operated manually or automatically, including operation controlled by a computer program.

Figure 3:
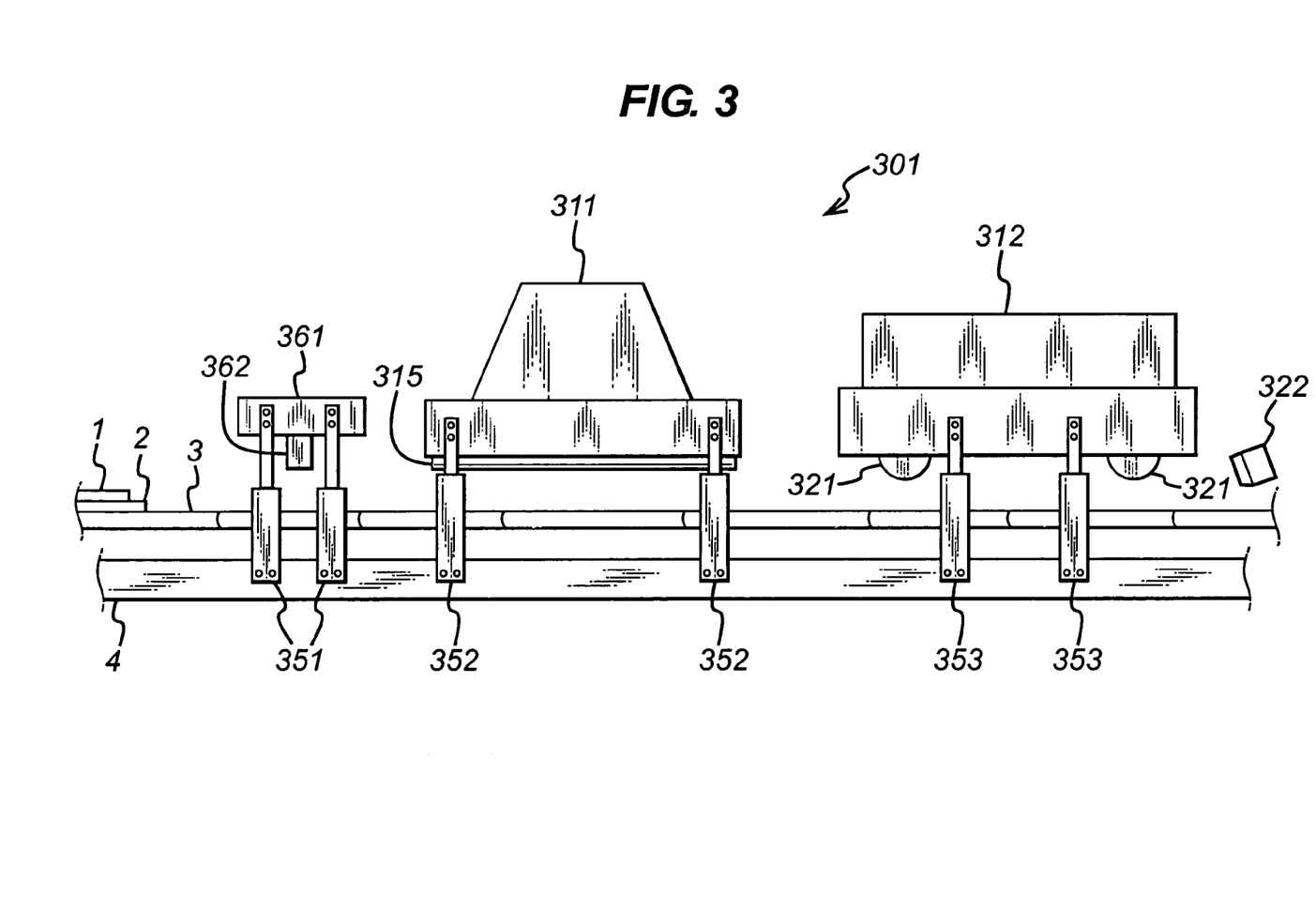
FIG. 3 is a side view of an embodiment of a cleaning assembly, also including optional measurement assembly.

FIG. 3 shows a side view of one embodiment of a cleaning assembly 301. Tray 2 can be moved along track 3 to bring surface of floor tile 1 underneath scrubber 312. Scrubber 312 extends across the width of cleaning assembly 301 and is supported by actuators 353 on the near side (shown) and on the far side (not shown). While surface of floor tile 1 is underneath scrubber 312, actuators 353 can be operated to lower scrubber 312 so that rollers 321 contact surface of floor tile 1. Rollers 321 can be rotated. Also, scrubber 312 has one or more outlets to dispense an aqueous detergent solution onto surface of floor tile 1. The tray 2 may be moved along track 3 while surface of floor tile 1 is in contact with rotating rollers 321.

After scrubbing is finished, scrubber 312 is raised so that rollers 321 are not in contact with floor tile 1. Optionally, excess cleaning fluid may be removed from the bottom of scrubber 312 by operating air knife 322. Such removal, if performed, may prevent undesirable dripping of cleaning fluid onto floor tile 1, as floor tile 1 passes underneath scrubber 312. Air knife 322 is supported by structural members (not shown) and is supplied with compressed air by a source of compressed air (not shown).

Also shown in FIG. 3 is burnisher 311, which extends across the width of service assembly 301 and is supported by actuators 352 on the near side (shown) and on the far side (not shown). Tray 2 can be moved along track 3 to bring surface of floor tile 1 underneath burnisher 311. Burnisher 311 extends across the width of cleaning assembly 301 and is supported by actuators 352 on the near side (shown) and on the far side (not shown). While surface of floor tile 1 is underneath burnisher 311, actuators 352 can be operated to lower burnisher 311 so that burnishing pad 315 contacts surface of floor tile 1. Burnishing pad 315 can be rotated. The tray 2 may be moved along track 3 while surface of floor tile 1 is in contact with rotating burnishing pad 315.

Also shown in FIG. 3 is a measurement assembly, which contains gloss meter 362 attached to mover 361. Mover 361 allows gloss meter 362 to be moved horizontally from the near side to the far side and back. Mover 361 is held in place by actuators 351 on the near side (shown) and the far side (not shown). The tray 2 can be moved along track 3 to any desired location: the mover 361 can be moved to any desired position; and the actuators 351 can be operated to lower gloss meter 362 until it is in proper position to measure the gloss of the portion of surface of floor tile 1 that is directly underneath gloss meter 362. In this way, a measurement can be made of the gloss of any specific portion of surface of floor tile 1. It is contemplated that multiple measurements of gloss may be made, including replicate measurements at one or more specific portion of surface of floor tile 1 as well as measurements at multiple portions of surface of floor tile 1.

Each of the items in cleaning assembly 301 may be operated manually or automatically, including operation controlled by a computer program.

Each of the items in FIG. 2 and FIG. 3 and FIG. 4 that is held up by one or more actuators is normally held up high enough above track 3 so that tray 2 and surface of floor tile 1 can move freely underneath that item. The actuators may be operated, when desired, to bring the item close to or into contact with surface of floor tile 1.

It is to be understood that for purposes of the present specification and claims that the range and ratio limits recited herein can be combined. For example, if ranges of 60 to 120 and 80 to 110 are recited for a particular parameter, it is understood that the ranges of 60 to 110 and 80 to 120 are also contemplated. As a further, independent, example, if a particular parameter is disclosed to have suitable minima of 1, 2, and 3, and if that parameter is disclosed to have suitable maxima of 9 and 10, then all the following ranges are contemplated: 1 to 9, 1 to 10, 2 to 9, 2 to 10, 3 to 9, and 3 to 10.

EXAMPLES

The method that was used for determining gloss is described in "Annual Book of ASTM Standards", Section 15, Volume 15.04, Test Procedure ASTM D 1455. A Gardner Byk Micro-Tri-Gloss meter, catalog number 4520, was used to record 60-degree gloss. In the case of the automated wear tester the gloss meter was fitted to a "robotic" arm that through the control program of the machine measured the gloss of the coated substrates.

Floor Tests at Grocery Store

The floor test areas were stripped of residual polish and repolished in the typical janitorial procedure as follows:

The floors were dust mopped to remove loose dirt, a 650 mL (22 oz) per 3.78 Liters (one gallon) of water solution of commercial stripper solution ("Airkem Air Strip" Airkem Professional Products, Division of Ecolab Inc., Mississauga, Ont. Canada L4W 2X5) was applied by string mop at a rate of ca. 1,000 square feet/gallon (25 m2/l); after a five minute soak period, the floors were scrubbed with a 431 mm (17 inch) black stripping floor pad (3M Company, St. Paul, Minn. 55144; "7200 Black Stripper Pad" on a 175 rpm floor machine (Howell Electric Motors, Plainfield, N.J., model 88400-026); the stripped floors were thoroughly rinsed twice by damp mopping with clear water, and allowed to dry. The stripped floors were divided into 4.65 m2 (50 square foot) sections perpendicular to the normal direction of floor traffic flow. To each of the sections four coats of polish to be tested were applied, with a "FastTrack" White/Blue, Finish Medium cotton/rayon string mop No. 24011, Hillyard, St. Joseph Mo. 64502 at a rate of about 50 m2/l (2,000 square feet/gallon). Each coat was allowed to dry for one hour before the next coat was applied. Coatings were applied (4 coats) to floors composed of homogenous vinyl composition tiles, and cured at ambient conditions.

After the coatings had cured at ambient conditions for a specific time, the floors were opened to pedestrian traffic. The floor test areas were exposed to foot traffic (approximately 25,000 persons/week) as well as wheeled traffic from shopping carts, maintenance carts, sample trays, etc. The 60-degree gloss was measured every five days after a sufficient exposure to traffic, machine auto scrubbing with detergent solution, and burnishing maintenance was performed on the test floors in the typical janitorial fashion as follows:

The floors were dust mopped to remove loose dirt; the floors were machined scrubbed with a Pioneer Eclipse PE-1700 Automatic Scrubber equipped with a Pro Link FBR 17-K 431 mm (17 in) Red 40-D pad, Pro-Link Inc. Canton Mass. 02021. The cleaning solution charged to the Pioneer Eclipse PE-1700 Automatic Scrubber was a Airkem Floor Cleaner Neutral Cleaner at 15 mL(0.5 oz.) per 3.78 L (one gallon) water. The burnishing machine used was a SpeedStar Pioneer ST21K WA Pionner Eclipse Corporation, Sparta, N.C. 28675 fitted with a 21 inch UHS Natural Synthetic Pad (3M Company, St. Paul, Minn. 55101 "Scotch Brite" Ultra High Speed Tan Buffer Pad) on a 2000 rpm propane floor burnishing machine. The test floors were exposed to two passes of the auto scrubber and burnishing machines, five times per week, for a period of 60 days.

Composition of test Soil Used in Accelerated Wear Tester.

50% by weight of "Dust for Industrial Testing No. 11" (Supplied by Japan Association of Powder process industry & Engineering, in Kyoto, Japan), plus 50% by weight of Recipe-1

Recipe-1:

8 g Raven 14 Carbon Black Powder (supplied by Colombian Chemical) 1000 g of Celite™ 281 (flux calcined diatomaceous earth (supplied by Celite Corporation).

"Dust for Industrial Testing No. 11" has the Following Composition:

| Ingredient | % by weight |
|---|---|
| $SiO_2$ | 34 to 40 |
| $Fe_2O_3$ | 17 to 23 |
| $Al_2O_3$ | 26 to 32 |
| CaO | 0 to 3 |
| MgO | 3 to 7 |
| $TiO_2$ | 0 to 4 |

The particle size distribution of Dust for Industrial Testing No. 11 was as follows:

| size | % by weight |
|---|---|
| larger than 1 micrometer | 60 to 70 |
| larger than 2 micrometer | 45 to 55 |
| larger than 4 micrometer | 17 to 27 |
| larger than 6 micrometer | 3 to 13 |
| larger than 8 micrometer | 0 to 6 |

Coating Application for exposure to Accelerated Wear Tester:

The method for applying the floor polish coating to substrates for testing purposes is described in "Annual Book of ASTM Standards," Section 15, Volume 15.04, Test Procedure ASTM D 1436 (2000), Test Method B.

Four coats of finish with about 1 hour dry time between coats Tiles were allowed to equilibrate for at least 24 hr before processing p First data corresponds to gloss measurement before any processing.

Accelerated Wear Tester Maintenance Settings/Conditions:
Dirt Cycle: Floor speed=25.4 cm/sec (10 inches/sec);
Amount of Dirt=1 to 2 grams of dirt per tile
Tile size=30.48 cm×30.48 cm (12 inch×12 inch)

Soil Cycle:
  Air pressure driving roller pin=128 kPa (20 psi)
  Total force bearing on roller pin=9.1 kg force (30 lb)
  Roller cycle=5 passes under the roller at 12.7 cm/sec (5 inch/sec)
Scuff Cycle: Wheel speed=1,000 rpm; Floor Speed: 38.1 cm/sec (15 inches/sec)
Wet Cycle: Sprinkle water on surface of tiles; 25.4 cm/sec (10 inches/sec)
Clean Cycle: Airkem Floor Cleaner Neutral Cleaner at 15 mL(0.5 oz.) per 3.78 L (one gallon) water; 25.4 cm/sec (10 inches/sec)
Burnish: RPM=2000; Pad=3M Gorilla™ Pad; floor speed: 45.7 cm/sec (18 inches/sec)
Gloss Measurement: at end of every five cycles 10 measurements/per tile: Average number reported.

There is a 3 minute hold after burnishing and a 5 minute dry time after cleaning.

Scuff Wheel Composition: Polyurethane cast over Iron Core (Durometer Hardness: 90A)

Formulation of Coatings Based on Zinc Modified Emulsions.

The formulation of the emulsion polymers of this invention is done in the manner common to floor polish formulating practices. The ingredients used, and their proportions and manner of addition are the same as is commonly practiced with conventional technology emulsion polymers.

Aqueous Floor Polish Formulation 1 for Polymer 1 (Order of Addition Shown; Amounts are Parts by Weight)

| Material | Function | Amount |
|---|---|---|
| Water | diluent | 31.28 |
| Masurf FS-230 (1%)[1] | wetting agent | 2.50 |
| Kathon CG/ICP (1.5%)[2] | biocide | 0.03 |
| SE-213 | defoamer | 0.02 |
| RHOPLEX 1531 (38%)[2]2 | alkali soluble/swellable resin | 2.89 |
| Diethylene Glycol Ethyl Ether | coalescent | 3.14 |
| Dipropylene Glycol Methyl Ether | coalescent | 2.99 |
| Kodalflex TXIB | plasticizer | 1.50 |
| Tributoxy Ethyl Phosphate | leveling aid | 2.12 |
| Polymer 1; Emulsion (39%) | vehicle | 47.46 |
| Chemcor 325G (35%)[4] | polyethylene wax emulsion | 3.24 |
| Chemcor 43G40 (40%)[4] | polypropylene wax emulsion | 2.83 |
| Total | | 100.00 |

Notes:
[1]Mason Chemical Co. (Arlington Heights, IL)
[2]Rohm and Haas Co. (Philadelphia, PA)
[3]Wacker Silicones Corp. (Adrian, MI)
[4]ChemCor. (Chester, NY)

Formulation Constants:

| Polymer/ASR/Wax Ratio | 85/5/10 |
|---|---|
| Theoretical Non-Volatile Solids | 25.5% |

Aqueous Floor Polish Formulation 2 for Polymer 2 (Order of Addition Shown; Amounts are Parts by Weight)

| Material | Function | Amount |
|---|---|---|
| Water | diluent | 29.51 |
| Masurf FS-230 (1%)[1] | wetting agent | 1.25 |
| Kathon CG/ICP (1.5%)[2] | biocide | 0.03 |
| SE-213 | defoamer | 0.04 |
| RHOPLEX 1531 (38%)[2] | alkali soluble/swellable resin | 2.89 |
| Diethylene Glycol Ethyl Ether | coalescent | 3.14 |
| Dipropylene Glycol Methyl Ether | coalescent | 2.99 |
| Tributoxy Ethyl Phosphate | leveling aid | 1.50 |
| Eastman TXIB | plasticizer | 1.50 |
| Polymer 2; Emulsion (36.6%) | vehicle | 51.09 |
| Chemcor 325G (35%)[4] | polyethylene wax emulsion | 3.23 |
| Chemcor 43G40 (40%)[4] | polypropylene wax emulsion | 2.83 |
| TOTAL | | 100.00 |

Notes:
[1]Mason Chemical Co. (Arlington Heights, IL)
[2]Rohm and Haas Co. (Philadelphia, PA)
[3]Wacker Silicones Corp. (Adrian, MI)
[4]ChemCor. (Chester, NY)

Formulation Constants:

| Polymer/ASR/Wax Ratio | 85/5/10 |
|---|---|
| Theoretical Non-Volatile Solids | 25% |

Aqueous Floor Polish Formulation 3 for Polymer 3 (Order of Addition Shown; Amounts are Parts by Weight)

| Material | Function | Amount |
|---|---|---|
| Water | diluent | 31.02 |
| Masurf FS-230 (1%)[1] | wetting agent | 0.86 |
| Kathon CG/ICP (1.5%)[2] | biocide | 0.03 |
| SE-213 | defoamer | 0.02 |
| ACRYSOL 644 (42%)[2] | alkali soluble/swellable resin | 5.43 |
| Diethylene Glycol Ethyl Ether | coalescent | 5.69 |
| Tripropylene Glycol Methyl Ether | coalescent | 1.00 |
| Tributoxy Ethyl Phosphate | leveling aid | 1.77 |
| Polymer 3; Emulsion (38%) | vehicle | 45.02 |
| Chemcor 325 N (35%)[4] | polyethylene wax emulsion | 4.89 |
| Chemcor 43 N (40%)[4] | polypropylene wax emulsion | 4.28 |
| Total | | 100.00 |

Notes:
[1] Mason Chemical Co. (Arlington Heights, IL)
[2] Rohm and Haas Co. (Philadelphia, PA)
[3] Wacker Silicones Corp. (Adrian, MI)
[4] ChemCor. (Chester, NY)

Formulation Constants:

| Polymer/ASR/Wax Ratio | 75/10/15 |
|---|---|
| Theoretical Non-Volatile Solids | 24.6% |

Aqueous Floor Polish Formulation 4 for Polymer 4 (Order of Addition Shown; Amounts in Parts by Weight)

| Material | Function | Amount |
|---|---|---|
| Water | diluent | 32.41 |
| Masurf FS-230 (1%)[1] | wetting agent | 0.75 |
| Kathon CG/ICP (1.5%)[2] | biocide | 0.03 |
| SE-213 | defoamer | 0.02 |
| Diethylene Glycol Ethyl Ether | coalescent | 5.0 |
| Dipropylene Glycol Methyl Ether | coalescent | 1.25 |
| Dibutyl Phthalate | plasticizer | 1.25 |
| Tributoxy Ethyl Phosphate | leveling aid | 2.50 |
| Polymer 4; Emulsion (38%) | vehicle | 45.83 |
| Chemrez 30 (30%)[4] | Alkali-soluble resin | 3.54 |
| A-C ®-325 N (35%)[4] | polyethylene wax emulsion | 4.13 |
| Epolene ® E-43 N (40%)[4] | polypropylene wax emulsion | 3.29 |
| Total | | 100.00 |

Notes:
[1] Mason Chemical Co. (Arlington Heights, IL)
[2] Rohm and Haas Co. (Philadelphia, PA)
[3] Wacker Silicones Corp. (Adrian, MI)
[4] ChemCor. (Chester, NY)

Formulation Constants:

| Polymer/ASR/Wax Ratio | 82/5/13 |
|---|---|
| Theoretical Non-Volatile Solids | 25% |

Polymer 1: A polymer latex was prepared with a monomer composition of 31 BA/20.5 MMA/20 ST/17 BMA/11.5 MAA following the technology taught in U.S. Pat. No. 4,517,330. The latex composition further contains 2.4% $Zn^{++}$ on latex solids, added as $Zn(NH_3)_4(HCO_3)_2$ and 1.33% $K^+$ on latex solids, added as KOH. Final latex solids was 39% and final pH was 8.6.

Polymer 2: A polymer latex was prepared with a monomer composition of 28 BA/27 MMA/35 STY/10 MAA following the technology taught in U.S. Pat. No. 4,517,330, except that no KOH was added. The latex composition further contains 2.2% $Zn^{++}$ on latex solids, added as $Zn(NH_3)_4(HCO_3)_2$. Example 2 was formulated into the test composition as described in formulation 1B. Final latex solids was 36.6%; final pH was 8.5

Polymer 3: A polymer latex was prepared with a monomer composition of 28 BA/52 MMA/12 STY/8 MAA according to the technology taught in U.S. Pat. No. 4,517,330, except that no KOH was added. The latex composition further contains 2.1% $Zn^{++}$ on latex solids, added as $Zn(NH_3)_4(HCO_3)_2$. Final latex solids: 38.0%; final pH=9.3.

Polymer 4: Polymer prepared according to the technology taught in U.S. Pat. No. 4,517,330 except that no KOH was added. A polymer latex was prepared with a monomer composition of 35BA/9MMA/40ST/16MAA. The latex composition further contains 2.5% $Zn^{++}$ on latex solids, added as $Zn(NH_3)_4(HCO_3)_2$. Final latex solids: 38.0%; final pH=9.0

TABLE 1

AUTOMATIC WEAR TESTER DATA: 60 Degree Gloss Data (Average of 10 readings)

| Floor Polish Polymer | Formulation 1 Polymer 1 | Formulation 2 Polymer 2 |
|---|---|---|
| Initial | 87 | 88 |
| 5 cycles | 56 | 63 |
| 10 cycles | 65 | 70 |
| 15 cycles | 64 | 57 |
| 20 cycles | 59 | 40 |
| 25 cycles | 50 | 27 |
| 30 cycles | 45 | 26 |

Total time from start of test to end of test was 7.5 hours.

TABLE 2

GROCERY STORE (SUPERMARKET) DATA: 60 Degree Gloss Data (Average of 10 readings)

| Floor Polish Polymer | Formulation 1 Polymer 1 | Formulation 2 Polymer 2 |
|---|---|---|
| Initial | 87 | 88 |
| 1 day | 79 | 80 |
| 3 days | 73 | 76 |
| 6 days | 73 | 79 |
| 10 days | 75 | 76 |
| 12 days | 74 | 76 |
| 19 days | 69 | 65 |
| 22 days | 74 | 67 |
| 28 days | 59 | 60 |
| 31 days | 66 | 59 |
| 35 days | 67 | 50 |
| 45 days | 60 | 52 |
| 50 days | 58 | 47 |
| 60 days | 59 | 45 |

Time from start of test to end of test: 1440 hours

TABLE 3

AUTOMATIC WEAR TESTER DATA: 60 Degree Gloss Data
(Average of 10 readings)

| Floor Polish Polymer | Formulation 3 Polymer 3 | Formulation 4 Polymer 4 |
|---|---|---|
| Initial | 79 | 88 |
| 5 cycles | 49 | 45 |
| 10 cycles | 56 | 50 |
| 15 cycles | 60 | 52 |
| 20 cycles | 53 | 41 |
| 25 cycles | 50 | 38 |
| 30 cycles | 46 | 35 |

Total time from start of test to end of test was 7.5 hours.

TABLE 4

GROCERY STORE (SUPERMARKET) DATA: 60 Degree Gloss Data
(Average of 10 readings)

| Floor Polish Polymer | Formulation 3 Polymer 3 | Formulation 4 Polymer 4 |
|---|---|---|
| Initial | 86 | 82 |
| 1 day | 76 | 75 |
| 3 days | 70 | 73 |
| 6 days | 70 | 68 |
| 10 days | 69 | 65 |
| 12 days | 68 | 62 |
| 19 days | 69 | 65 |
| 22 days | 70 | 67 |
| 28 days | 59 | 53 |
| 31 days | 66 | 60 |
| 35 days | 65 | 58 |
| 45 days | 60 | 50 |
| 50 days | 63 | 50 |
| 60 days | 65 | 50 |

Time from start of test to end of test: 1440 hours

Based on the results using the Accelerated Wear Tester, the rank order of the Formulations was as follows:

| No. of cycles | Best | Second Best | Third Best | Worst |
|---|---|---|---|---|
| 0 | F2, F4[1] | | F1 | F3 |
| 5 | F2 | F1 | F3 | F4 |
| 10 | F2 | F1 | F3 | F4 |
| 15 | F1 | F3 | F2 | F4 |
| 20 | F1 | F3 | F4 | F2 |
| 25 | F1, F3[1] | | F4 | F2 |
| 30 | F3 | F1 | F4 | F2 | note
[1]Tie

Based on the results on the Grocery Floor, the rank order of the Formulations was as follows:

| No. of days | Best | Second Best | Third Best | Worst |
|---|---|---|---|---|
| 0 | F2 | F1 | F3 | F4 |
| 1 | F2 | F1 | F3 | F4 |
| 3 | F2 | F1, F4[1] | | F3 |
| 6 | F2 | F1 | F3 | F4 |
| 10 | F2 | F1 | F3 | F4 |
| 12 | F1 | F2 | F3 | F4 |
| 19 | F1, F3[1] | | F2, F4[1] | |
| 22 | F1 | F2 | F3, F4[1] | |
| 28 | F2 | F1, F3[1] | | F4 |
| 31 | F1, F3[1] | | F4 | F2 |
| 35 | F1 | F3 | F4 | F2 |
| 45 | F1, F3[1] | | F2 | F4 |
| 50 | F3 | F1 | F4 | F2 |
| 60 | F3 | F1 | F4 | F2 | note
[1]Tie

The Accelerated Wear Tester, after 30 cycles (7.5 hours) ranks the floor polishes in the same order as the results of the Grocery Floor testing (60 days).

We claim:

1. An apparatus for producing stress on a surface, said apparatus comprising one or more service assembly and one or more cleaning assembly,
    (a) wherein said service assembly comprises one or more means for applying dirt to said surface, and, additionally comprises means for applying water to said surface, and
    (b) wherein said cleaning assembly comprises one or more scrubber, or one or more burnisher, or a combination thereof.

2. The apparatus of claim 1, further comprising one or more means for measuring the quality of said surface.

3. The apparatus of claim 1, wherein said service assembly comprises one or more means for scuffing said surface.

4. The apparatus of claim 1, wherein said cleaning assembly comprises one or more scrubber and one or more burnisher.

5. The apparatus of claim 1, wherein said surface is flooring material.

6. The apparatus of claim 1, wherein said surface is a substrate with a coating.

7. The apparatus of claim 1, further comprising means for independently controlling the exposure of said surface to said service assembly and the exposure of said surface to said cleaning assembly.

8. A method of testing a surface with the apparatus of claim 1 comprising the steps of
    (i) one or more times, using said service assembly to apply dirt to said surface, and
    (ii) one or more times, using said cleaning assembly to scrub said surface, or to burnish said surface, or a combination thereof.

9. The method of claim 8 comprising the steps of
    (i) one or more times, using said service assembly to apply dirt to said surface and to scuff said surface, and
    (ii) one or more times, using said cleaning assembly to scrub said surface and to burnish said surface.

10. The method of claim 8, further comprising the step of measuring the quality of said surface before said steps (a) and (b) and the step of measuring the quality of said surface after said steps (a) and (b).

11. The apparatus of claim 1, wherein said service assembly comprises one or more means for scuffing said surface, wherein said means for scuffing said surface comprises means for bringing an object made of rubber into contact with said surface.

12. The apparatus of claim 1, wherein said service assembly additionally comprises a tool that applies mechanical force to push said dirt into closer contact with said surface, to drag said dirt along said surface, or any combination thereof.

13. The apparatus of claim 1, wherein said service assembly applies said water and said dirt to said surface in such a way that said water is present in contact with said surface at the same time as said dirt.

14. The apparatus of claim 1, wherein said surface is smooth.

15. The apparatus of claim 14, wherein said surface comprises a coating on vinyl, linoleum, or other resilient material.

16. The apparatus of claim 14, wherein said cleaning assembly comprises one or more burnisher.

17. The apparatus of claim 1, wherein said surface is moved horizontally on straight tracks.

\* \* \* \* \*